United States Patent
Himeda

(10) Patent No.: US 10,393,679 B2
(45) Date of Patent: Aug. 27, 2019

(54) OPERATION GUIDE SYSTEM FOR X-RAY ANALYSIS, OPERATION GUIDE METHOD THEREFOR, AND OPERATION GUIDE PROGRAM THEREFOR

(71) Applicant: Rigaku Corporation, Akishima-shi, Tokyo (JP)

(72) Inventor: Akihiro Himeda, Akishima (JP)

(73) Assignee: RIGAKU CORPORATION, Akishima-Shi, Tokyo (JP)

( * ) Notice: Subject to any disclaimer, the term of this patent is extended or adjusted under 35 U.S.C. 154(b) by 274 days.

(21) Appl. No.: 15/598,821

(22) Filed: May 18, 2017

(65) Prior Publication Data

US 2017/0336333 A1 Nov. 23, 2017

(30) Foreign Application Priority Data

May 18, 2016 (JP) .................................. 2016-099916

(51) Int. Cl.
| | |
|---|---|
| *G01N 23/201* | (2018.01) |
| *G01N 23/20* | (2018.01) |
| *G01N 23/207* | (2018.01) |
| *G01N 23/20016* | (2018.01) |

(52) U.S. Cl.
CPC .......... *G01N 23/20* (2013.01); *G01N 23/207* (2013.01); *G01N 23/20016* (2013.01); *G01N 2223/052* (2013.01); *G01N 2223/303* (2013.01); *G01N 2223/408* (2013.01); *G01N 2223/61* (2013.01)

(58) Field of Classification Search
USPC ............................................ 378/6, 7, 86–90
See application file for complete search history.

(56) References Cited

U.S. PATENT DOCUMENTS 5,600,303 A * 2/1997 Husseiny ................ F41H 11/12
340/568.1
6,215,847 B1 * 4/2001 Perrins ................... A61L 2/0035
250/453.11
(Continued)

FOREIGN PATENT DOCUMENTS

JP       H08101204 A     4/1996
JP       3353496 B2     12/2002
(Continued)

*Primary Examiner* — Irakli Kiknadze
(74) *Attorney, Agent, or Firm* — Cantor Colburn LLP

(57) ABSTRACT

Provided are operation guide system for X-ray analysis to enable users to easily understand measurement of X-ray optical system to be selected. The operation guide system includes: measurement information acquisition unit for acquiring information on a sample and each X-ray measurement optical system part; sample magnification acquisition unit for acquiring magnification for display; incident X-ray shape deformation unit for determining distorted shape of an incident X-ray obtained by magnifying shape of the incident X-ray based on the magnification in a plane perpendicular to an optical axis direction; scattered X-ray shape deformation unit for determining distorted shape of a scattered X-ray obtained by magnifying shape of the scattered X-ray based on the magnification in the plane; and X-ray measurement optical system modeling unit for modeling a deformed shape of the sample, the distorted shape of the incident X-ray, and the distorted shape of the scattered X-ray.

9 Claims, 14 Drawing Sheets

(56) References Cited

U.S. PATENT DOCUMENTS

| | | | | |
|---|---|---|---|---|
| 9,001,969 B2 * | 4/2015 | Murakoshi | ........... | A61B 6/4233 378/70 |
| 2008/0056452 A1 * | 3/2008 | Sasaki | .................. | G01N 23/207 378/204 |
| 2013/0138382 A1 | 5/2013 | Mitsunaga | | |

FOREIGN PATENT DOCUMENTS

| | | |
|---|---|---|
| JP | 2013137297 A | 7/2013 |
| JP | 2013137298 A | 7/2013 |

* cited by examiner

FIG.4

SELECT ANALYSIS PURPOSE

○ QUALITATIVE/QUANTITATIVE ANALYSIS AND STRUCTURAL ANALYSIS OF POWDERED OR POLYCRYSTAL SAMPLE
○ QUALITATIVE/QUANTITATIVE ANALYSIS AND STRUCTURAL ANALYSIS OF THIN-FILM SAMPLE
● ANALYSIS OF FILM THICKNESS, DENSITY, AND INTERFACE ROUGHNESS OF THIN-FILM SAMPLE
○ CRYSTALLINE EVALUATION AND STRUCTURE ANALYSIS OF EPITAXIAL FILM

[OK] [Cancel]

FIG.5

| INPUT SAMPLE INFORMATION | | | |
|---|---|---|---|
| SET VALUES FOR FILM STRUCTURE | | | |
| LAYER | COMPOSITION | DENSITY (g/cm3) | FILM THICKNESS (nm) |
| SECOND LAYER | GaAs | 4.23 | 50 |
| FIRST LAYER | InGaAs | 5.11 | 200 |
| SUBSTRATE | GaAs | 5.31 | — |

SAMPLE SIZE

LENGTH (mm) 10.0   WIDTH(mm) 8.0
THICKNESS(mm) 0.50

OK   Cancel

FIG.6

MEASUREMENT CONDITIONS

THICKNESS OF THICKEST LAYER 200 nm

OPTICAL SYSTEM: HIGH-RESOLUTION PARALLEL BEAM/ LIGHT-RECEIVING SLIT OPTICAL SYSTEM ▼

SLIT CONDITIONS:

| INCIDENT SLIT | LIGHT-RECEIVING SLIT1 | LIGHT-RECEIVING SLIT2 |
|---|---|---|
| 0.5 mm | 0.2 mm | 0.2 mm |

SCAN CONDITIONS:

SCAN AXIS: 2θ/ω

| MODE | START ANGLE | END ANGLE |
|---|---|---|
| STEP | 0.0000° | 6.0000° |

| STEP | SPEED | ATTENUATOR |
|---|---|---|
| 0.0060° | 0.6000°/min | AUTOMATIC |

OK    Cancel

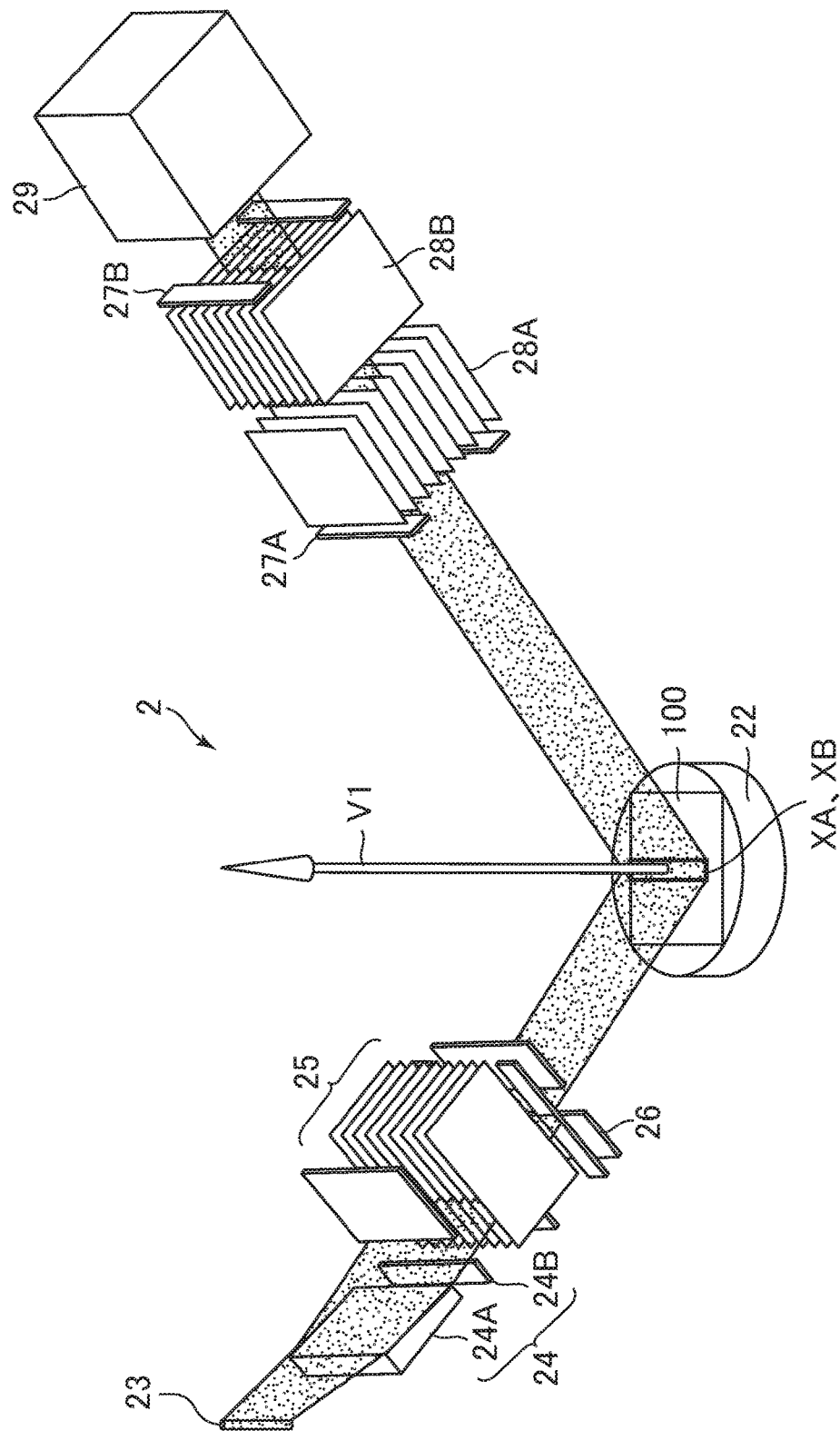

OPERATION GUIDE SYSTEM FOR X-RAY ANALYSIS, OPERATION GUIDE METHOD THEREFOR, AND OPERATION GUIDE PROGRAM THEREFOR

CROSS-REFERENCE TO RELATED APPLICATION

The present invention claims priority under 35 U.S.C. § 119 to Japanese application JP 2016-099916, filed on May 18, 2016, the content of which is hereby incorporated by reference into this application.

BACKGROUND OF THE INVENTION

1. Field of the Invention

The present invention relates to an operation guide system for X-ray analysis, an operation guide method therefor, and an operation guide program therefor, and more particularly, to a guidance function for a user.

2. Description of the Related Art

In recent years, with the development of an X-ray analysis apparatus, a wide variety of users use the X-ray analysis apparatus for various analysis purposes. The X-ray analysis apparatus is no longer an apparatus used only by some skilled users, but is increasing in the opportunity of being used by users inexperienced in the X-ray analysis apparatus.

SUMMARY OF THE INVENTION

When measurement is performed through use of an X-ray analysis apparatus, it is desired that a user select parts suitable for a sample to be analyzed, assemble a measurement optical system, and perform measurement under a control condition suitable for the sample. However, it is difficult for the user inexperienced in the X-ray analysis apparatus to determine those operations in his/her own judgment.

In Japanese Patent No. 3353496, there is disclosed an analysis apparatus including setting means capable of the setting of setting data required for various kinds of analysis processing with a simple operation based on information obtained by collecting a setting procedure for data required for each of a plurality of pieces of analysis processing.

In JP 2013-137297A and JP 2013-137298A, there are disclosed X-ray analysis apparatus that have functions of realizing a plurality of measuring methods and enable effective utilization of those measuring functions.

However, unlike a visible light optical system, in an X-ray optical system, a user cannot confirm how an X-ray propagates. Further, in regard to dimensions of the X-ray optical system, in general, the dimensions of both a sample and a cross section of the X-ray are small. When selecting an X-ray optical system, it is difficult for the user to understand how incident X-rays for irradiating the sample irradiates the sample, and how a detector detects scattered X-rays which are generated from the sample, even when an operation guide system displays a state of measuring the sample.

The present invention has been made in view of the above-mentioned problems, and has an object to provide an operation guide system for X-ray analysis, an operation guide method therefor, and an operation guide program therefor, which enable a user to easily understand measurement of an X-ray optical system to be selected.

In order to solve the above-mentioned problems, an operation guide system for X-ray analysis according to one embodiment of the present invention includes: measurement information acquisition means for acquiring information on a sample, and information on each of a plurality of X-ray measurement optical system parts configured to conduct X-ray analysis on the sample; sample magnification acquisition means for acquiring a magnification by which the sample is to be magnified for display; incident X-ray shape deformation means for determining a distorted shape of an incident X-ray obtained when the sample is measured through use of the plurality of X-ray measurement optical system parts; scattered X-ray shape deformation means for determining a distorted shape of a scattered X-ray obtained when the sample is measured through use of the plurality of X-ray measurement optical system parts; and X-ray measurement optical system modeling means for modeling a deformed shape of the sample, which is obtained by magnifying a shape of the sample based on the magnification, the distorted shape of the incident X-ray, and the distorted shape of the scattered X-ray, in which the distorted shape of the incident X-ray is a shape obtained by magnifying a shape of an incident X-ray, which irradiates the sample, based on the magnification in a plane perpendicular to an incident optical axis direction of the incident X-ray, and in which the distorted shape of the scattered X-ray is a shape obtained by magnifying a shape of a scattered X-ray, which is generated from the sample to be detected, based on the magnification in a plane perpendicular to a scattered optical axis direction of the scattered X-ray.

In the operation guide system for X-ray analysis according to Item (1), the operation guide system may further include propagating X-ray shape determination means for determining, based on the information on the sample and the information on each of the plurality of X-ray measurement optical system parts acquired by the measurement information acquisition means, the shape of the incident X-ray which irradiates the sample and the shape of the scattered X-ray which is generated from the sample to be detected, which are obtained when the sample is measured through use of the plurality of X-ray measurement optical system parts. The incident X-ray shape deformation means may be configured to magnify, based on the magnification, the shape of the incident X-ray determined by the propagating X-ray shape determination means in the plane perpendicular to the incident optical axis direction of the incident X-ray, to thereby determine the distorted shape of the incident X-ray. The scattered X-ray shape deformation means may be configured to magnify, based on the magnification, the shape of the scattered X-ray determined by the propagating X-ray shape determination means in the plane perpendicular to the scattered optical axis direction of the scattered X-ray, to thereby determine the distorted shape of the scattered X-ray.

In the operation guide system for X-ray analysis according to Item (1) or (2), the plurality of X-ray measurement optical system parts may include a first incident-side optical part arranged closest to the sample on an incident side of the sample, and a first scattered-side optical part arranged closest to the sample on a scattered side of the sample. The operation guide system for X-ray analysis further may include: first incident-side optical part shape deformation means for determining a distorted shape of the first incident-side optical part, the distorted shape being obtained by magnifying a shape of the first incident-side optical part based on the magnification in the plane perpendicular to the incident optical axis direction of the incident X-ray; and first scattered-side optical part shape deformation means for determining a distorted shape of the first scattered-side optical part, the distorted shape being obtained by magnifying a shape of the first scattered-side optical part based on the magnification in the plane perpendicular to the scattered optical axis direction of the scattered X-ray. The X-ray measurement optical system modeling means may be further configured to model the distorted shape of the first incident-side optical part and the distorted shape of the first scattered-side optical part.

In the operation guide system for X-ray analysis according to Item (1), the operation guide system may further include optical part shape deformation means for determining each of distorted shapes of the plurality of X-ray measurement optical system parts, the distorted shapes being obtained by magnifying respective shapes of the plurality of X-ray measurement optical system parts based on the magnification in a plane perpendicular to an optical axis direction of an X-ray which propagates through the plurality of X-ray measurement optical system parts. The incident X-ray shape deformation means may be configured to determine the distorted shape of the incident X-ray based on the information on the sample acquired by the measurement information acquisition means and the distorted shapes of the plurality of X-ray measurement optical system parts determined by the optical part shape deformation means. The scattered X-ray shape deformation means may be configured to determine the distorted shape of the scattered X-ray based on the information on the sample acquired by the measurement information acquisition means and the distorted shapes of the plurality of X-ray measurement optical system parts determined by the optical part shape deformation means.

In the operation guide system for X-ray analysis according to any one of Items (1) to (4), the incident X-ray shape deformation means may be configured to maintain the shape of the incident X-ray in the incident optical axis direction of the incident X-ray, and the scattered X-ray shape deformation means may be configured to maintain the shape of the scattered X-ray in the scattered optical axis direction of the scattered X-ray.

In the operation guide system for X-ray analysis according to any one of Items (1) to (5), the operation guide system may further include sample angular placement information acquisition means for acquiring information on an angular placement of the sample. The incident X-ray shape deformation means may be configured to determine the distorted shape of the incident X-ray further based on the information on the angular placement. The scattered X-ray shape deformation means may be configured to determine the distorted shape of the scattered X-ray further based on the information on the angular placement.

An operation guide method for X-ray analysis according to one embodiment of the present invention may include: a measurement information acquisition step of acquiring information on a sample and information on each of a plurality of X-ray measurement optical system parts configured to conduct X-ray analysis on the sample; a sample magnification acquisition step of acquiring a magnification by which the sample is to be magnified for display; an incident X-ray shape deformation step of determining a distorted shape of an incident X-ray obtained when the sample is measured through use of the plurality of X-ray measurement optical system parts; a scattered X-ray shape deformation step of determining a distorted shape of a scattered X-ray when the sample is measured through use of the plurality of X-ray measurement optical system parts; and an X-ray measurement optical system modeling step of modeling a deformed shape of the sample, which is obtained by magnifying a shape of the sample based on the magnification, the distorted shape of the incident X-ray, and the distorted shape of the scattered X-ray. The distorted shape of the incident X-ray may be a shape obtained by magnifying a shape of an incident X-ray, which irradiates the sample, based on the magnification in a plane perpendicular to an incident optical axis direction of the incident X-ray. The distorted shape of the scattered X-ray may be a shape obtained by magnifying a shape of a scattered X-ray, which is generated from the sample to be detected, based on the magnification in a plane perpendicular to a scattered optical axis direction of the scattered X-ray.

An operation guide program for X-ray analysis according to one embodiment of the present invention may cause a computer to function as: measurement information acquisition means for acquiring information on a sample, and information on each of a plurality of X-ray measurement optical system parts configured to conduct X-ray analysis on the sample; sample magnification acquisition means for acquiring a magnification by which the sample is to be magnified for display; incident X-ray shape deformation means for determining a distorted shape of an incident X-ray obtained when the sample is measured through use of the plurality of X-ray measurement optical system parts; scattered X-ray shape deformation means for determining a distorted shape of a scattered X-ray obtained when the sample is measured through use of the plurality of X-ray measurement optical system parts; and X-ray measurement optical system modeling means for modeling a deformed shape of the sample, which is obtained by magnifying the sample based on the magnification, the distorted shape of the incident X-ray, and the distorted shape of the scattered X-ray. The distorted shape of the incident X-ray may be a shape obtained by magnifying a shape of an incident X-ray, which irradiates the sample, based on the magnification in a plane perpendicular to an incident optical axis direction of the incident X-ray. The distorted shape of the scattered X-ray may be a shape obtained by magnifying a shape of a scattered X-ray, which is generated from the sample to be detected, based on the magnification in a plane perpendicular to a scattered optical axis direction of the scattered X-ray.

According to the present invention, the operation guide system for X-ray analysis, the operation guide method therefor, and the operation guide program therefor, which enable a user to easily determine a measurement condition for a sample to be analyzed, are provided.

BRIEF DESCRIPTION OF THE DRAWINGS

FIG. 4 is a diagram for illustrating an analysis purpose selection screen according to the first embodiment of the present invention.

FIG. 5 is a diagram for illustrating a sample information input screen according to the first embodiment of the present invention.

FIG. 6 is a diagram for illustrating a measurement condition screen according to the first embodiment of the present invention.

FIG. 10A is a display image according to the first embodiment of the present invention.

DETAILED DESCRIPTION OF THE INVENTION

Figure 1:
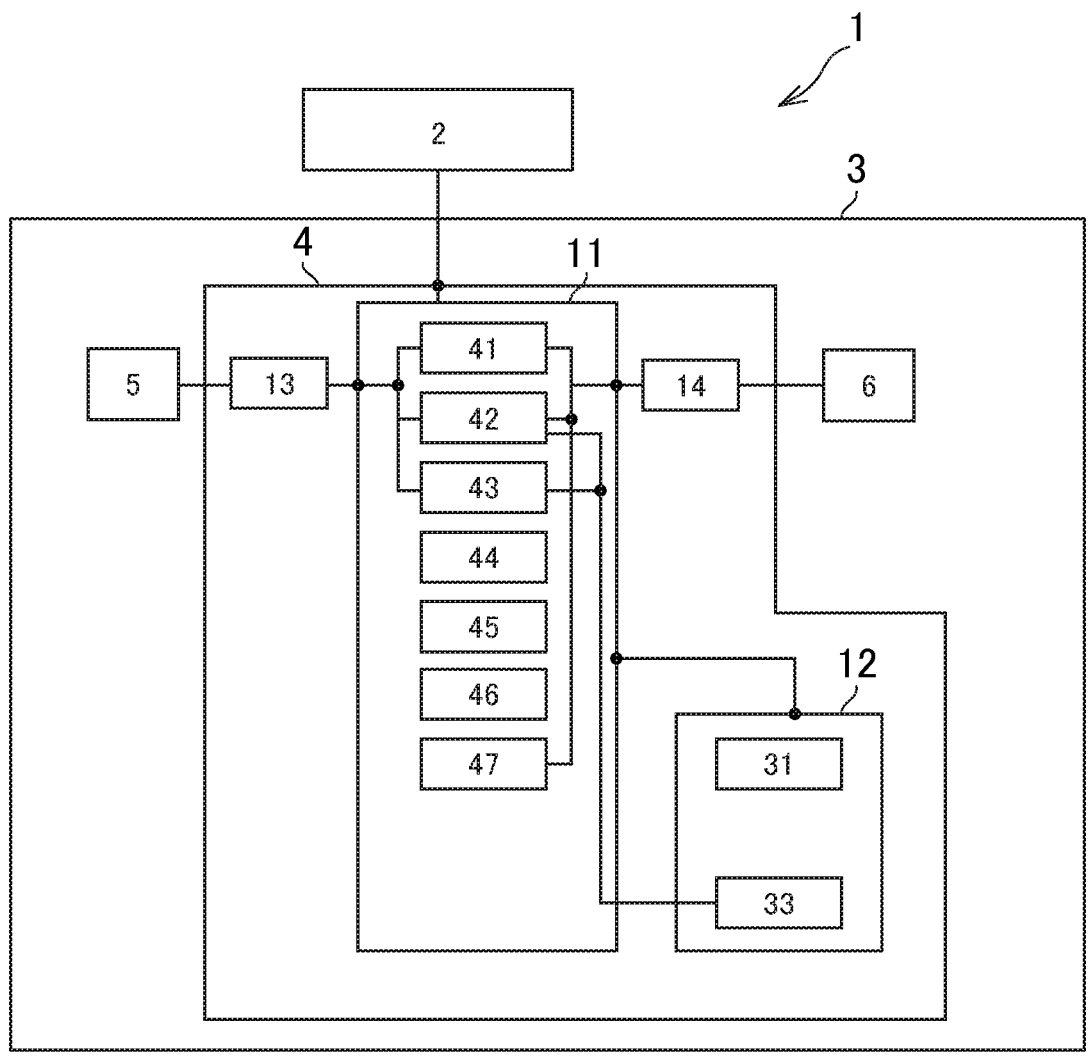
FIG. 1 is a block diagram for illustrating a configuration of an X-ray analysis apparatus according to a first embodiment of the present invention.

Now, embodiments of the present invention are described referring to the drawings. For clearer illustration, some dimensions, shapes, and the like are schematically illustrated in the drawings in comparison to actual ones. However, the dimensions, the shapes, and the like are merely an example, and do not limit understanding of the present invention. Further, herein and in each of the drawings, like elements as those described relating to the drawings already referred to are denoted by like reference symbols, and detailed description thereof is sometimes omitted as appropriate.

First Embodiment

FIG. 1 is a block diagram for illustrating a configuration of an X-ray analysis apparatus 1 according to a first embodiment of the present invention. The X-ray analysis apparatus 1 according to the first embodiment includes an X-ray measuring unit 2 (X-ray measurement optical system) and an operation guide system 3, and the operation guide system 3 includes a control unit 4, an input device 5, and a display device 6. The control unit 4 includes a CPU section 11, a storage section 12, an information input portion 13, and an information output portion 14. The control unit 4 is achieved by a computer used in general, and further includes a read only memory (ROM) (not shown) and a random access memory (RAM) (not shown). The ROM and the RAM form internal memories of the computer. The storage section 12 is a recording medium, and may be formed of a semiconductor memory, a hard disk drive, or other such arbitrary recording medium. In this case, the storage section 12 is installed inside the computer, but may be installed outside the computer. The storage section 12 may be a single recording medium, or may be formed of a plurality of recording mediums. The information input portion 13 is, for example, an interface connected to the input device 5, and is configured to acquire, from the input device 5, information input to the input device 5 by a user. The information output portion 14 is, for example, an interface connected to the display device 6, and is configured to output, to the display device 6, information to be displayed on the display device 6. The input device 5 is achieved by a keyboard and a mouse, a touch panel, or the like, and the display device 6 is achieved by a display or the like used in general. The control unit 4 of the X-ray analysis apparatus 1 includes respective means for executing respective steps of an operation guide method for X-ray analysis described below. Further, an operation guide program for X-ray analysis according to the first embodiment is a program for causing the computer to function as the respective means. The CPU section 11 and the storage section 12 of the control unit 4 are described below in detail.

Figure 2:
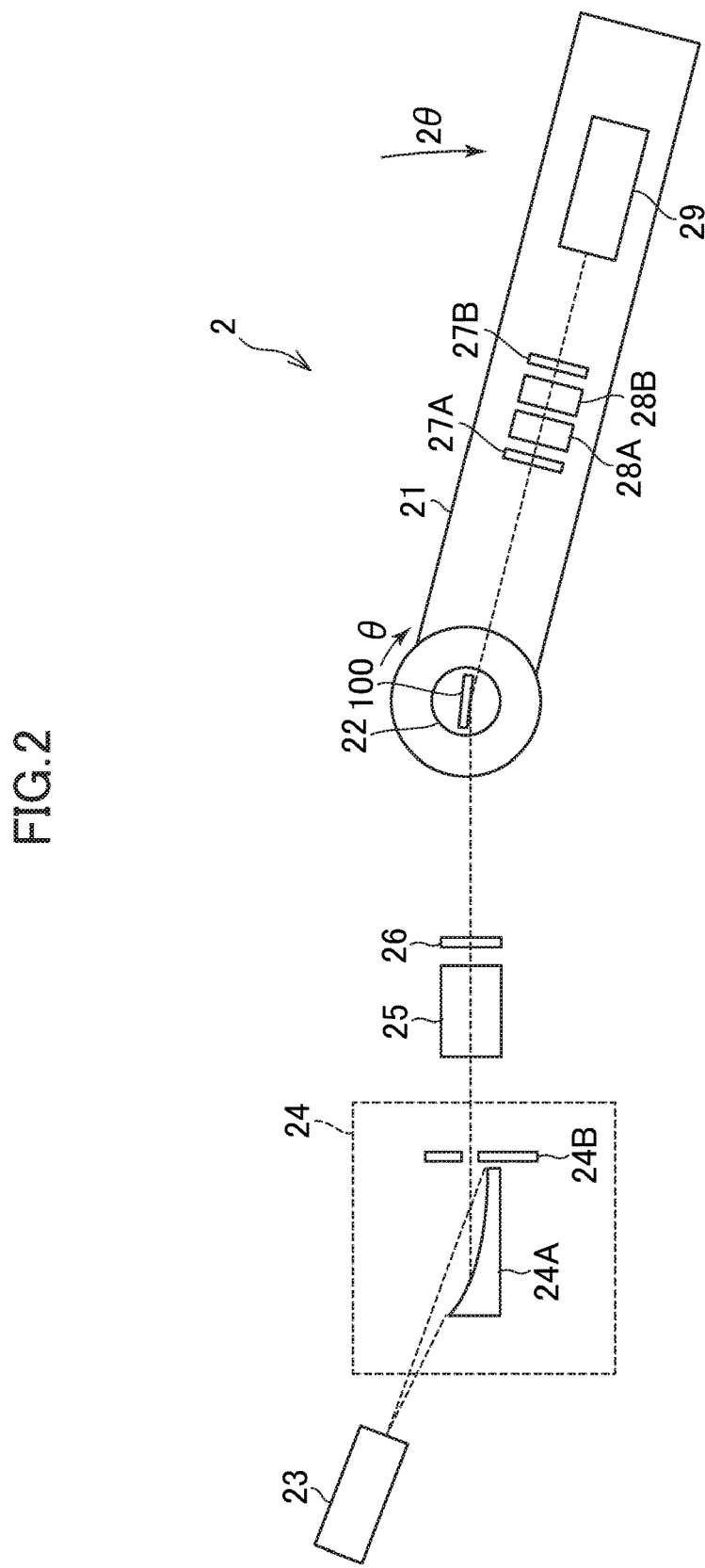
FIG. 2 is a block diagram for illustrating an example of an X-ray measuring unit of the X-ray analysis apparatus according to the first embodiment of the present invention.

FIG. 2 is a block diagram for illustrating an example of the X-ray measuring unit 2 of the X-ray analysis apparatus 1 according to the first embodiment. The X-ray measuring unit 2 illustrated in FIG. 2 includes a plurality of X-ray measurement optical system parts configured to conduct X-ray analysis on a sample. In FIG. 2, the X-ray measuring unit 2 is a parallel beam optical system used in X-ray reflectometry (XRR) measurement, and is configured to irradiate a sample 100 with incident X-rays and detect scattered X-rays generated from the sample 100. In the X-ray reflectometry measurement, the scattered X-rays become reflected X-rays by being reflected by the sample. In X-ray diffraction measurement, the scattered X-rays become diffracted X-rays generated from the sample. The scattered X-rays generated from the sample herein includes X-rays respectively generated during various X-ray analyses. Here, the sample 100 is obtained by laminating one or more layers of thin films on a substrate and, in the first embodiment, has a film structure in which two layers of thin films are formed on a substrate. As illustrated in FIG. 2, the plurality of X-ray measurement optical system parts included in the X-ray measuring unit 2 include a goniometer 21, a support base 22 for supporting the sample 100, an X-ray generating portion 23, a cross beam optics (CBO) unit 24, an incident Soller slit 25, an incident slit 26, two light-receiving slits (a first light-receiving slit 27A and a second light-receiving slit 27B), a parallel slit analyzer (PSA) 28A, a light-receiving Soller slit 28B, and a detector 29.

The goniometer 21 is a θ-2θ rotation system, and the support base 22 is mounted on the goniometer 21 so that the sample 100 is located at a rotation center. The two light-receiving slits, the parallel slit analyzer 28A, the light-receiving Soller slit 28B, and the detector 29 are mounted on the goniometer 21 so as to be rotated by 2θ as the support base 22 is rotated by θ.

The X-ray generating portion 23 includes an X-ray tube (X-ray tube bulb), and is configured to emit X-rays to be diverged to a multilayer mirror 24A. The CBO unit 24 includes the multilayer mirror 24A and a selection slit 24B arranged behind the multilayer mirror 24A. Arrangement of the selection slit 24B in different positions makes it possible to easily switch between a focusing method and a parallel beam method. In the first embodiment, the parallel beam method is selected. The multilayer mirror 24A includes a reflection surface having a cross section being a parabola (quadratic function). The multilayer mirror 24A is arranged such that the focus of the parabola is included in the microfocus of the X-rays emitted by the X-ray generating portion 23. Of the X-rays reflected by the multilayer mirror 24A, X-rays having a predetermined wavelength are selectively reflected toward a predetermined direction due to the multilayer film structure of the multilayer mirror 24, and are collimated because the cross section of the reflection surface is a parabola, to thereby enter the incident Soller slit 25.

The X-ray that has passed through the incident Soller slit 25 and the incident slit 26 enters the sample 100 placed on the support base 22 by an incident angle θ as incident X-rays. In this case, the incident angle θ represents an angle formed between the optical axis of the incident X-rays and the surface of the sample 100 (surface of a film structure), and is different from the case of geometrical optics that defines the incident angle as an angle formed between an incident light beam and the normal to a reflection surface. The incident X-rays are applied to the sample 100, and the reflected X-rays are emitted from the sample 100 with a reflection angle θ (angle formed between the optical axis of the reflected X-rays and the surface of the sample 100). An angle between the reflected X-rays and the incident X-rays is 2θ.

The reflected X-rays passes through the first light-receiving slit 27A, the parallel slit analyzer 28A, the light-receiving Soller slit 28B, and the second light-receiving slit 27B in that order, to enter the detector 29 and be detected by the detector 29. The parallel slit analyzer 28A is formed of thin metal plates stacked on top of one another at equal intervals, and hence it is possible to improve resolution by arranging a beam and a metal foil in parallel. The light-receiving Soller slit 28 is arranged by rotating the parallel slit analyzer by 90°, and can reduce asymmetry of an X-ray peak. The resolution of the measurement optical system is determined by characteristics of the X-ray generating portion 23 and the CBO unit 24, as well as a width of the incident slit 26, a width of each of the two light-receiving slits, an interval between the two light-receiving slits, and respective characteristics of the incident Soller slit 25, the parallel slit analyzer 28A, and the light-receiving Soller slit 28B. As illustrated in FIG. 2, the X-ray measuring unit 2 is a parallel beam optical system called a high-resolution optical system. When resolution as high as that of the high-resolution optical system is not required, the incident Soller slit 25 may be removed. In order to enable measurement at a resolution higher than that of the high-resolution optical system, a channel monochromator (one channel cut crystal (one pair of channel cut crystals)) may be provided in place of the incident Soller slit 25. In order to enable measurement at an even higher resolution, a 4-crystal monochromator (two channel cut crystals (two pairs of channel cut crystals)) may be provided. Further, an analyzer crystal may be provided in place of the parallel slit analyzer 28A and the light-receiving Soller slit 28B.

The detector 29 may be anyone of a zero-dimensional detector (for example, counter tube), a one-dimensional detector (for example, linear CCD sensor), and a two-dimensional detector (for example, CCD sensor). In this case, the detector 29 is a counter tube.

[Operation Guide]

Next, a description is made of the operation guide method for the X-ray analysis apparatus 1 (or the operation guide system 3) according to the first embodiment. As illustrated in FIG. 1, the storage section 12 stores a control program 31, and includes a system information storage portion 33.

Figure 3:
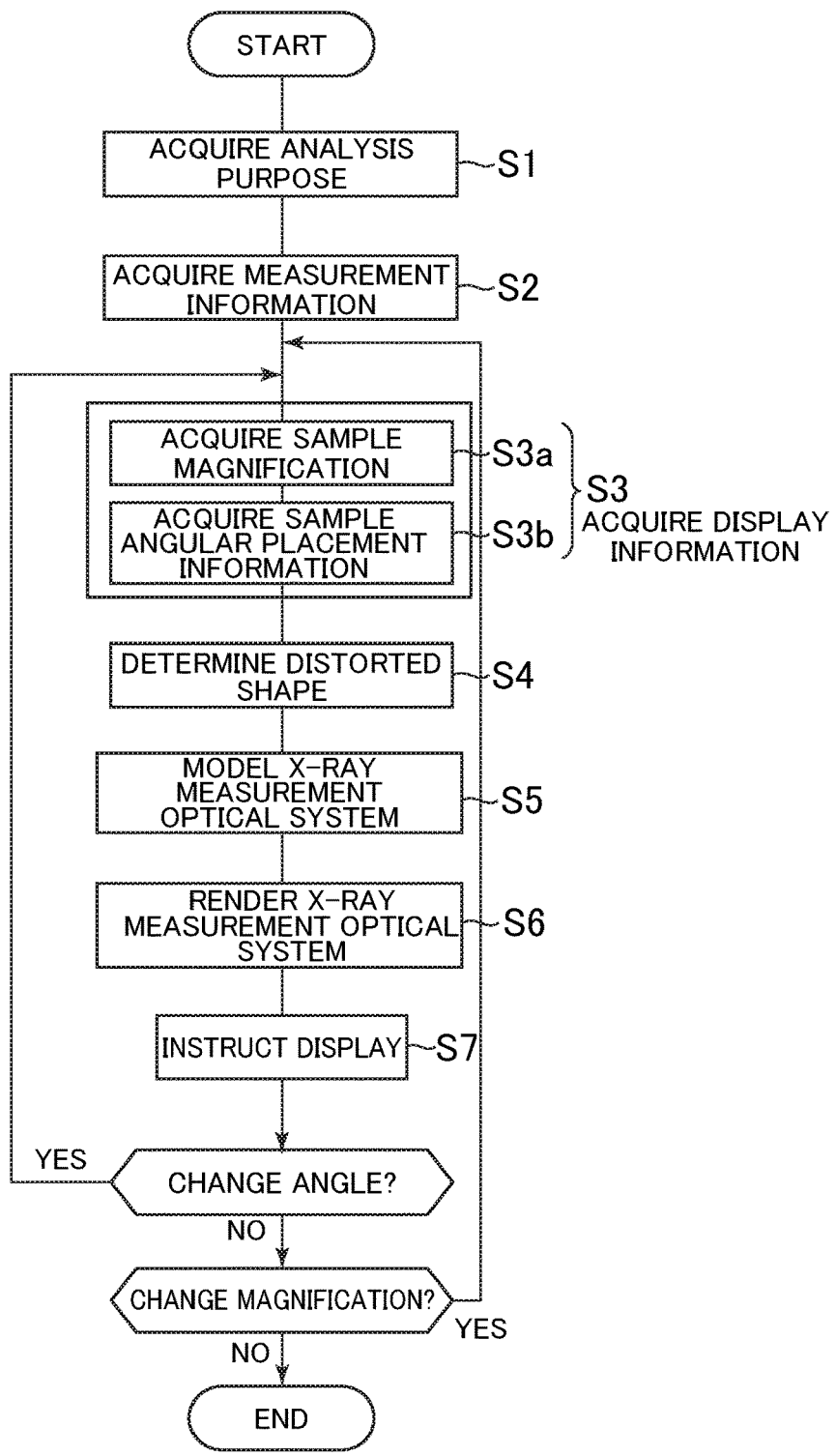
FIG. 3 is a flowchart of a control program according to the first embodiment of the present invention.

FIG. 3 is a flowchart of the control program 31 according to the first embodiment. The control program 31 is a program executed before measurement, and is used for displaying a state of the X-ray measurement optical system to be selected as an image to the user so that the user can easily understand the state. The X-ray analysis apparatus 1 according to the first embodiment is able to conduct different types of analysis corresponding to a plurality (M, where M is a natural number) of analysis purposes. As illustrated in FIG. 1, the CPU section 11 of the control unit 4 includes an analysis purpose acquisition portion 41, a measurement information acquisition portion 42, a display information acquisition portion 43, a distorted shape determination portion 44, an X-ray measurement optical system modeling portion 45, an X-ray measurement optical system rendering portion 46, and a display instruction portion 47.

[S1: Analysis Purpose Acquisition Step]

When the control program 31 is started, the information output portion 14 of the control unit 4 causes the display device 6 to display an analysis purpose selection screen. The information input portion 13 of the control unit 4 acquires information input by the input device 5 including a mouse. The analysis purpose acquisition portion 41 acquires the analysis purpose selected by the user as a predetermined analysis purpose (S1: analysis purpose acquisition step).

FIG. 4 is a diagram for illustrating the analysis purpose selection screen according to the first embodiment. As illustrated in FIG. 4, the X-ray analysis apparatus 1 according to the first embodiment is capable of analyses for four (M=4) analysis purposes, and the four analysis purposes are displayed on the analysis purpose selection screen. The user selects an analysis purpose from among the four analysis purposes. In this case, the user uses the mouse to select "analysis of film thickness, density, and interface roughness of thin-film sample" (hereinafter referred to as "first analysis purpose") as an example, and clicks the OK button. The information input portion 13 of the control unit 4 acquires the information input by the user through use of the input device 5 (first analysis purpose), and the procedure advances to the subsequent step. When the analysis purpose selection screen does not include the analysis purpose desired by the user, the user clicks the cancel button. In this case, the control program 31 is ends.

[S2: Measurement Information Acquisition Step]

The measurement information acquisition portion 42 acquires the information on the sample and the information on the plurality of X-ray measurement optical system parts configured to conduct X-ray analysis on the sample (S2: measurement information acquisition step). The information on the sample includes information on the shape and size of the sample. The information on the X-ray measurement optical system parts includes some or all of the function, the shape, the placement location, and other features of the parts.

Specifically, the measurement information acquisition step is carried out as follows. The information output portion 14 of the control unit 4 displays a sample information input screen on the display device 6. The user inputs information on a sample for which measurement with a predetermined analysis purpose is to be performed by the X-ray measuring unit 2. The measurement information acquisition portion 42 acquires the information on the sample input by the user via the information input portion 13.

FIG. 5 is a diagram for illustrating the sample information input screen according to the first embodiment. The user uses the keyboard to input the information on the sample being a target of the analysis purpose, and uses the mouse to click the OK button. When the information on the user's sample is not information that can be input to the sample information input screen, the user clicks the cancel button. In this case, the control program 31 ends.

Here, measurement with the first analysis purpose is X-ray reflectometry (XRR). The sample being the target of the analysis purpose is a thin-film sample, and is formed by stacking a plurality of layers on the surface of a substrate. The information on the sample includes design values of the film structure of the thin-film sample and the size (length, width, and thickness) of the sample. The film structure includes: the composition (in this case, GaAs) and the density of the substrate; and the composition, the density, and the film thickness of the respective layers to be stacked (in this case, two thin films formed of a first layer of InGaAs and a second layer of GaAs). The thin-film sample to be the target of the analysis purpose is rarely a completely unknown sample, and in general, setting values for forming the thin-film sample are known. Therefore, by acquiring those pieces of information as the sample information, it is possible to use the sample information for the determination of a measurement condition and image formation of the X-ray measurement optical system.

When the measurement information acquisition portion 42 acquires the information on the sample, the control unit 4 derives a recommended X-ray measurement optical system based on the information on the sample input by the user and the information on the plurality of X-ray measurement optical system parts stored in the system information storage portion 33. Then, the information output portion 14 of the control unit 4 causes the display device 6 to display a measurement condition screen. When the user agrees with the recommended X-ray measurement optical system, the user selects the recommended X-ray measurement optical system. The measurement information acquisition portion 42 acquires which system the selected X-ray measurement optical system is via the information input portion 13 to acquire the information on the plurality of X-ray measurement optical system parts forming the X-ray measurement optical system from the system information storage portion 33.

FIG. 6 is a diagram for illustrating the measurement condition screen according to the first embodiment. FIG. 6 is a diagram for illustrating recommended measurement conditions and includes the measurement conditions in addition to the information on the plurality of X-ray measurement optical system parts. A high-resolution optical system (high-resolution parallel beam/light-receiving slit optical system) is illustrated in FIG. 6. Slit conditions determined by the sample size and scan conditions corresponding to the high-resolution optical system are displayed in parallel. When the user wants to perform measurement with the recommended measurement conditions, the user clicks the OK button. As a result, the information input portion 13 of the control unit 4 acquires information on the fact that the user has clicked the OK button, and the measurement information acquisition portion 42 of the control unit 4 acquires the information on the plurality of X-ray measurement optical system parts in addition to the information on the sample.

The measurement conditions herein include a condition for an X-ray measurement optical system (hardware) including the plurality of X-ray measurement optical system parts, and a control condition (e.g., a scan condition) applied when measuring using the X-ray measurement optical system. However, the information on the X-ray measurement optical system to be acquired by the measurement information acquisition portion 42 only needs to include the information on the plurality of X-ray measurement optical system parts included in the X-ray measurement optical system.

When the user does not want to perform measurement with the recommended measurement conditions, the user can change each individual condition on the measurement condition screen to his/her desired measurement conditions and then click the OK button. Further, when the user cannot change the measurement conditions to his/her desired measurement conditions, the user clicks the cancel button. In this case, it is assumed that the user has not determined the measurement conditions, and hence the control program 31 ends.

Further, information on parts among the plurality of X-ray measurement optical system parts already assumed to be only one type may be directly acquired by the measurement information acquisition portion 42 from the system information storage portion 33. For example, when the X-ray generating portion 23 is one type, information on the X-ray generating portion 23 is directly acquired from the system information storage portion 33. The user may also select each part forming the X-ray measurement optical system based on his/her desire.

[S3: Display Information Acquisition Step]

The display information acquisition portion 43 acquires display information necessary for image display (S3: display information acquisition step). The display information acquisition portion 43 includes a sample magnification acquisition portion 43a and a sample angular placement information acquisition portion 43b. The display information acquisition step S3 according to the first embodiment includes a sample magnification acquisition step S3a of acquiring, by the sample magnification acquisition portion 43a, a magnification by which the sample is to be magnified for display, and a sample angular placement information acquisition step S3b of acquiring, by the sample angular placement information acquisition portion 43b, information on the angular placement of the sample.

Figure 7:
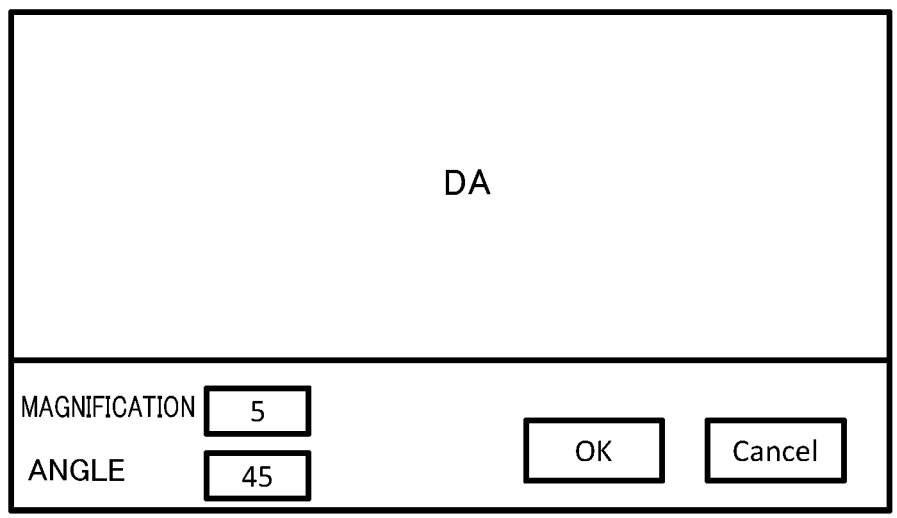
FIG. 7 is a diagram for illustrating a display information input screen according to the first embodiment of the present invention.

FIG. 7 is a diagram for illustrating a display information input screen according to the first embodiment. The display information input screen includes a display part DA, a magnification input window for inputting a magnification, and an angular placement input window for inputting the angular placement of the sample 100. Here, the measurement state of the X-ray measurement optical system can be displayed in the display part DA. The information output portion 14 of the control unit 4 causes the display device 6 to display the display information input screen. The user inputs the magnification by which the sample 100 is to be magnified for display and the angular placement of the sample 100 to the magnification input window and the angular placement input window, respectively, and clicks the OK button. The display information acquisition portion 43 of the control unit 4 acquires the magnification and the information on the angular placement. Here, for example, a=5, where a represents the magnification. Here, for example, an incident angle θ represents the information on the angular placement and θ=45°.

[S4: Distorted Shape Determination Step]

The distorted shape determination portion 44 determines a distorted shape of each of the plurality of X-ray measurement optical system parts, and a distorted shape of propagating X-rays that propagates through the X-ray measurement optical system, which is obtained when the sample is measured through use of the plurality of X-ray measurement optical system parts (S4: distorted shape determination step).

Figure 8:
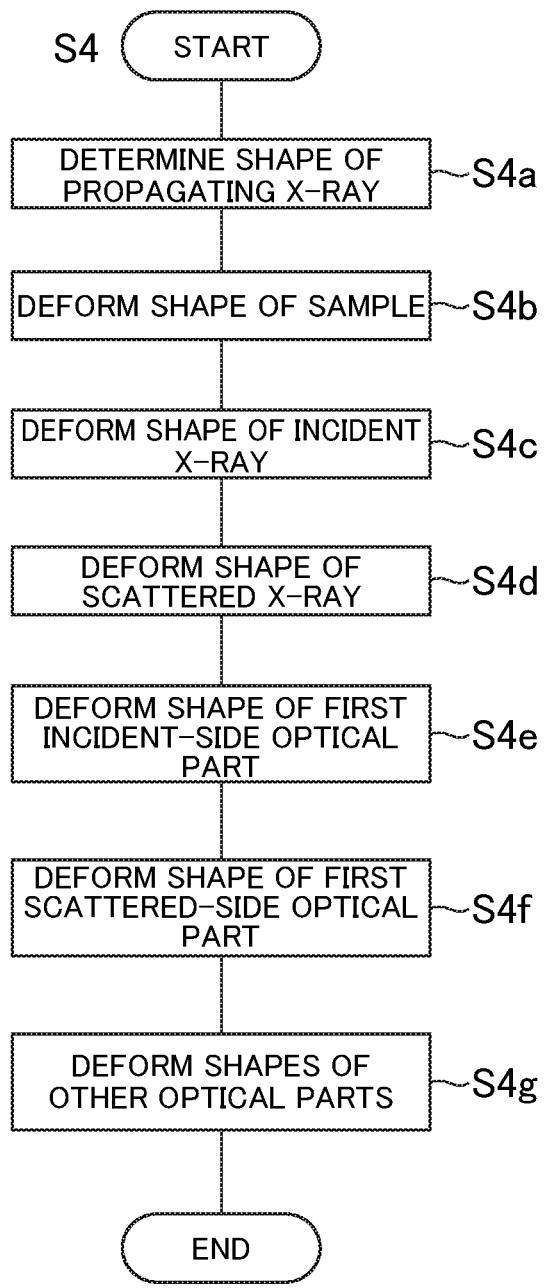
FIG. 8 is a flowchart of a distorted shape determination step according to the first embodiment of the present invention.

FIG. 8 is a flowchart of the distorted shape determining step S4 according to the first embodiment. The distorted shape determination portion 44 includes a propagating X-ray shape determination portion 44a, a sample shape deformation portion 44b, an incident X-ray shape deformation portion 44c, a scattered X-ray shape deformation portion 44d, a first incident-side optical part shape deformation portion 44e, a first scattered-side optical part shape deformation portion 44f, and an other optical part shape deformation portion 44g. The distorted shape determination step S4 according to the first embodiment includes a propagating X-ray shape determination step S4a, a sample shape deformation step S4b, an incident X-ray shape deformation step S4c, a scattered X-ray shape deformation step S4d, a first incident-side optical part shape deformation step S4e, a first scattered-side optical part shape deformation step S4f, and an other optical part shape deformation step S4g.

In the propagating X-ray shape determination step S4a, the propagating X-ray shape determination portion 44a determines, based on the information on the sample and the information on the plurality of X-ray measurement optical system parts acquired in the measurement information acquisition step S2, the shape of the propagating X-rays obtained when the sample is measured through use of the plurality of X-ray measurement optical system parts. The propagating X-ray shape determination portion 44a determines the shape of the propagating X-rays further based on the information on the angular placement of the sample acquired in the sample angular placement information acquisition step S3b. Here, the shape of the propagating X-rays includes the shape of the incident X-rays which irradiate the sample and the shape of the scattered X-rays to be detected, which is generated from the sample. In the first embodiment, the scattered X-rays are the reflected X-rays to be reflected by the sample 100. The distorted shape of the incident X-rays is a shape obtained by magnifying the shape of the incident X-rays based on the magnification in a plane perpendicular to an incident optical axis direction of the incident X-rays which irradiates the sample 100. The distorted shape of the scattered X-rays is a shape obtained by magnifying the shape of the scattered X-rays based on the magnification in a plane perpendicular to a scattered optical axis direction of the scattered X-rays to be detected, which is generated from the sample 100.

Here, the incident X-rays include all X-rays in a path in which the X-rays exit from the X-ray generating portion 23 to enter the sample 100. However, the incident X-rays only need to include at least an X-ray which enters the sample 100 of the X-rays in the path in which the X-rays exit from the X-ray generating portion 23 to enter the sample 100. It is desired that the incident X-rays include all X-rays propagating between the sample and a first incident-side optical part (here, the incident slit 26) arranged closest to the sample on an incident side of the sample.

The scattered X-rays include all X-rays in a path in which the X-rays are generated from the sample 100 and enter (a light-receiving window of) the detector 29 to be detected. However, the scattered X-rays only need to include at least the X-rays generated from the sample 100 (in this case, X-rays in a part reflected by the sample 100) of the X-rays in the path in which the X-rays are generated from the sample 100 and enter (the light-receiving window of) the detector 29 to be detected. It is desired that the scattered X-rays include all X-rays propagating between the sample and a first scattered-side optical part (here, the first light-receiving slit 27A) arranged closest to the sample on a scattered side of the sample. The scattered X-rays may correspond with the detector field of view and, in this case, is the X-ray which enters (the light-receiving window of) the detector 29 to be detected. The shape of the X-ray is described below.

Figure 9A:
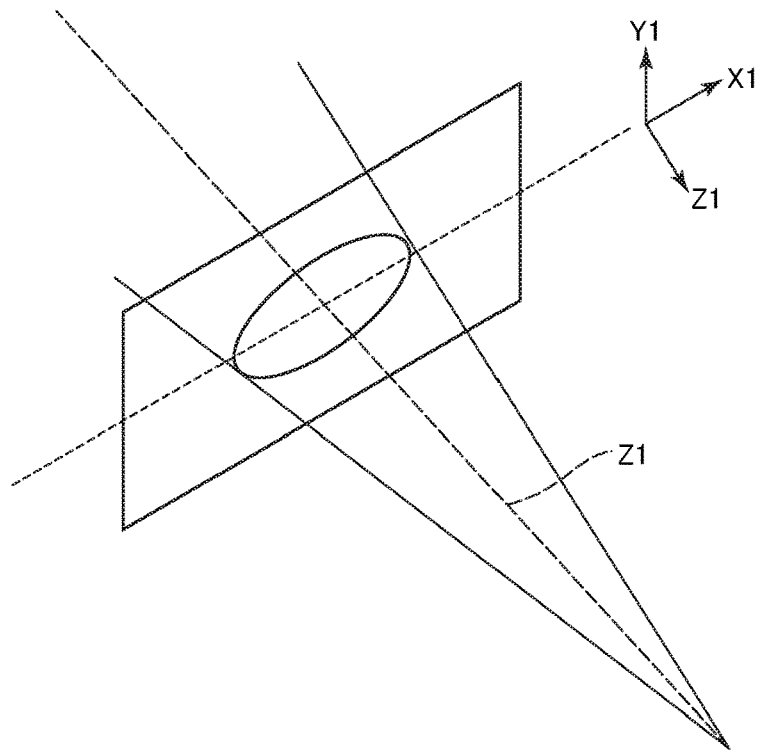
FIG. 9A is a diagram for schematically illustrating a shape of propagating X-rays.

FIG. 9A is a diagram for schematically illustrating the shape of the propagating X-rays according to the first embodiment. A direction in which an X-ray propagates through the X-ray measurement optical system is assumed to be an optical axis direction (Z1 direction) of the propagating X-rays. An optical axis Z1 of the propagating X-rays passes through a part having the highest intensity along the optical axis direction in a plane perpendicular to the optical axis Z1 of the propagating X-rays. In FIG. 9A, the plane (X1-Y1 plane) perpendicular to the optical axis Z1 of the propagating X-rays is illustrated.

Figure 9B:
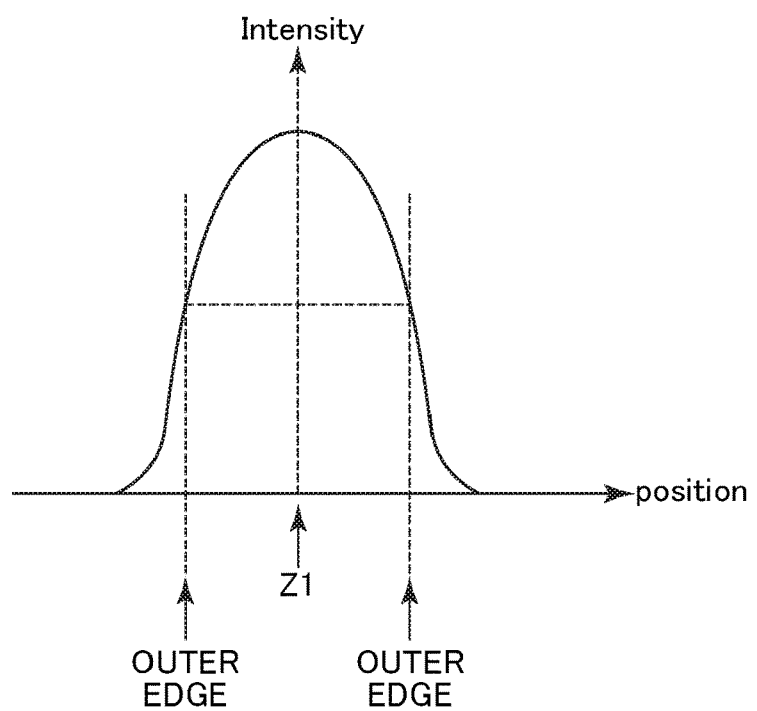
FIG. 9B is a graph for showing an intensity distribution of the propagating X-rays.

FIG. 9B is a graph for showing an intensity distribution of the propagating X-rays according to the first embodiment. The horizontal axis of FIG. 9B represents a position on a straight line passing through the optical axis Z1 in the plane (X1-Y1 plane) perpendicular to the optical axis Z1. The vertical axis of FIG. 9B represents intensity of the propagating X-rays at each position. The shape of the propagating X-rays has outer edges which a re parts having intensities corresponding to a predetermined ratio with respect to the intensity on the optical axis, and may be a shape obtained by connecting the outer edges along the optical axis. In FIG. 9B, parts having intensities corresponding to a half value of the intensity on the optical axis are the outer edges.

The shape of the incident X-rays is the shape of an X-ray among the X-rays that are emitted from the X-ray generating portion 23 that has passed through some of the X-ray measurement optical system parts to enter the sample 100. The shape of the incident X-rays includes an irradiation region in which the sample 100 (and the periphery thereof) is irradiated by the incident X-rays. The shape of the scattered X-rays is the shape of an X-ray among the scattered X-rays that are generated from the sample 100 that reaches the detector 29 after passing through some of the X-ray measurement optical system parts. The scattered X-rays may correspond with the detector field of view. In such a case, the shape of the scattered X-rays is the shape of an X-ray that enters (the light-receiving window of) the detector 29 to be detected. The shape of the scattered X-rays includes a detection region generated by the sample 100 (and the periphery thereof), and X-rays generated from the detection region are detected by the detector 29. The shape of the scattered X-rays is the shape of the X-ray generated from the detection region to be detected, and hence may differ from the shape of an X-ray actually generated at a certain angular placement. For example, when the scattered X-rays are diffracted X-rays generated from a single crystal, the shape of the scattered X-rays at a certain angular placement may not include any X-rays that are actually generated, or a part of the shape of the scattered X-rays may include an X-ray that is actually generated.

In the sample shape deformation step S4b, the sample shape deformation portion 44b magnifies the shape of the sample based on the magnification to determine the deformed shape of the sample. In the incident X-ray shape deformation step S4c, the incident X-ray shape deformation portion 44c determines the distorted shape of the incident X-rays, the distorted shape being obtained by magnifying the shape of the incident X-rays, which irradiates the sample, based on the magnification in the plane perpendicular to the incident optical axis direction of the incident X-rays. In the scattered X-ray shape deformation step S4d, the scattered X-ray shape deformation portion 44d determines the distorted shape of the scattered X-rays, the distorted shape being obtained by magnifying the shape of the scattered X-rays, which is generated by the sample, based on the magnification in the plane perpendicular to the scattered optical axis direction of the scattered X-rays. In the first embodiment, the scattered X-rays are the reflected X-rays, and the scattered optical axis direction is a reflected optical axis direction.

In the first incident-side optical part shape deformation step S4e, the first incident-side optical part shape deformation portion 44e determines the distorted shape of the first incident-side optical part, the distorted shape being obtained by magnifying the shape of the first incident-side optical part (here, the incident slit 26) based on the magnification in the plane perpendicular to the incident optical axis direction of the incident X-rays. The term "first incident-side optical part" refers to an X-ray measurement optical system part which is arranged closest to the sample on the incident side of the sample. In the first scattered-side optical part shape deformation step S4$f$, the first scattered-side optical part shape deformation portion 44$f$ determines the distorted shape of the first scattered-side optical part, the distorted shape being obtained by magnifying the shape of the first scattered-side optical part (here, the first light-receiving slit 27A) based on the magnification in the plane perpendicular to the scattered optical axis direction of the scattered X-rays. The term "first scattered-side optical part" refers to an X-ray measurement optical system part which is arranged closest to the sample on the scattered side of the sample. In the other optical part shape deformation step S4$g$, the other optical part shape deformation portion 44$g$ determines deformed shapes for each of the other X-ray measurement optical system parts.

Here, the magnification a is assumed to be 5 (a=5). In the first embodiment, the simplest and most desired deformed shape is as described below. In the sample shape deformation step S4$b$, the deformed shape of the sample 100 is obtained by isotropically magnifying the shape of the sample 100 by the magnification a. In the incident X-ray shape deformation step S4$c$, the distorted shape of the incident X-rays is obtained by magnifying the shape of the incident X-rays by the magnification a in the plane perpendicular to the incident optical axis direction, to thereby maintain the shape (keep the same scale) of the incident X-rays in the incident optical axis direction. In the scattered X-ray shape deformation step S4$d$, the distorted shape of the scattered X-rays is obtained by magnifying the shape of the scattered X-rays by the magnification a in the plane perpendicular to the scattered optical axis direction, to thereby maintain the shape (keep the same scale) of the scattered X-rays in the scattered optical axis direction.

In the first incident-side optical part shape deformation step S4$e$, the distorted shape of the first incident-side optical part (here, the incident slit 26) is obtained by magnifying the shape of the first incident-side optical part by the magnification a in the plane perpendicular to the incident optical axis direction, to thereby maintain the shape (keep the same scale) of the incident X-rays in the incident optical axis direction. In the first scattered-side optical part shape deformation step S4$f$, the distorted shape of the first scattered-side optical part (here, the first light-receiving slit 27A) is obtained by magnifying the shape of the first scattered-side optical part by the magnification a in the plane perpendicular to the scattered optical axis direction, to thereby maintain the shape (keep the same scale) of the first scattered-side optical part in the scattered optical axis direction.

In the other optical part shape deformation step S4$g$, the other X-ray measurement optical system parts are X-ray measurement optical system parts through which X-rays pass, and include the CBO unit 24, the incident Soller slit 25, the incident slit 26, the parallel slit analyzer 28A, the light-receiving Soller slit 28B, and the second light-receiving slit 27B. Each of the distorted shapes of the X-ray measurement optical system parts are obtained by magnifying the shape of the X-ray measurement optical system part by the magnification a in a plane perpendicular to the optical axis direction of an X-ray passing through the X-ray measurement optical system part, to thereby maintain the shape (keep the same scale) of the X-ray measurement optical system part in the optical axis direction. The shapes of the X-ray measurement optical system parts do not need to directly reflect actual shapes, and may each be shapes of main parts of the X-ray measurement optical system parts in order to facilitate the user's understanding. For example, the shape of the CBO unit 24 is determined only by the shape of the multilayer mirror 24A and the shape of the selection slit 24B.

The other X-ray measurement optical system parts further include the X-ray generating portion 23 configured to emit an X-ray, and the distorted shape of the X-ray generating portion 23 is obtained by magnifying the shape of the X-ray generating portion 23 by the magnification a in a plane perpendicular to an optical axis direction of an X-ray emitted from the X-ray generating portion 23, to thereby maintain the shape (keep the same scale) of the X-ray generating portion 23 in the optical axis direction. However, the distorted shape of the X-ray generating portion 23 may be a schematically distorted shape as long as the state of the X-ray emitted from the X-ray generating portion 23 can be understood. The other X-ray measurement optical system parts further include the detector 29 configured to receive and detect an X-ray, and the distorted shape of the detector 29 is obtained by magnifying the shape of the detector 29 by the magnification a in a plane perpendicular to an optical axis direction of an X-ray to be received by the detector 29, to thereby maintain the shape (keep the same scale) of the detector 29 in the optical axis direction. The distorted shape of the detector 29 may be a schematically distorted shape as long as the state of the X-ray to be received by the detector 29 can be understood. The distorted shape of the multilayer mirror 24A may also be approximately determined. The optical axis of an X-ray which enters the multilayer mirror 24A and the optical axis of an X-ray which is reflected by the multilayer mirror 24A do not match, however the angle they form is extremely small. Therefore, those optical axes are approximated to one optical axis, for example, a bisector of the above-mentioned angle. The distorted shape of the multilayer mirror 24A may be obtained by magnifying the shape of the multilayer mirror 24A by the magnification a in a plane perpendicular to an optical axis direction of those optical axes, to thereby maintain the shape (keep the same scale) of the multilayer mirror 24A in the optical axis direction of those optical axes.

The goniometer 21 is included in the X-ray measuring unit 2, but the goniometer 21 is omitted from an image displayed in the display part DA. Therefore, a distorted shape does not need to be determined for the goniometer 21. Further, the support base 22 is a part for supporting the sample 100 and is not an optical part through which an X-ray passes or propagates, and hence the shape of the support base 22 may be, for example, magnified isotropically based on the magnification a similarly to the deformed shape of the sample 100.

When the sample 100 is magnified by the magnification a, it is desired that the distorted shape of the propagating X-rays and each of the distorted shapes of the plurality of X-ray measurement optical system parts through which the X-rays propagate be magnified by the same magnification in the plane perpendicular to the optical axis direction. However, the present invention is not limited thereto, and the above-mentioned shapes may be magnified based on the magnification a. Here, the phrase "based on the magnification a" refers to a range which can be substantially approximated to the magnification a, and it is desired that the range be within ±20% of the magnification a, and more desired that the range be within ±10% of the magnification a.

Further, in the plane perpendicular to the optical axis direction, it is desired that the shapes be magnified isotropically, but the shapes do not necessarily need to be magnified isotropically as long as the magnification is carried out within the range based on the magnification a.

Further, the term "distorted shape" refers to a shape that has been deformed on a scale different to an actual scale to exaggerate (or emphasize) the shape in order to facilitate the user's recognition of the shape. Therefore, the plane perpendicular to the optical axis direction and the optical axis direction have a different ratio of deformation (magnification) to each other. Further, among all the distorted shapes according to the first embodiment, the simplest and therefore most desired distorted shape is obtained by magnifying the shape by the magnification a (a>1) in the plane perpendicular to the optical axis direction to maintain the shape (keep the same scale) in the optical axis direction. However, the distorted shapes according to the first embodiment include all cases in which a ratio of a length in the plane perpendicular to the optical axis direction to a length in the optical axis direction is the magnification a or the range based on the magnification a. As a result, a distorted shape magnified by 10 times in the plane perpendicular to the optical axis direction, and magnified by 2 times in the optical axis direction, has the ratio of the length in the plane perpendicular to the optical axis direction to the length in the optical axis direction of 5 times. When the distorted shapes are isotropically reduced to half their size, the distorted shapes are magnified by 5 times in the plane perpendicular to the optical axis direction to match distorted shapes maintaining the shapes (keeping the same scales) in the optical axis direction.

In the first embodiment, in the sample shape deformation step S4b, the deformed shape of the sample 100 is obtained by isotropically magnifying the shape of the sample 100 by the magnification a, but the present invention is not limited thereto. The sample being the target of the first analysis purpose is a thin-film sample, and the user is primarily interested in the surface (film) direction (2-dimensional surface) of the thin-film sample, and is not particularly interested in the thickness direction of the thin-film sample. Therefore, the deformed shape of the sample 100 does not need to be obtained by isotropically magnifying the shape of the sample 100 by the magnification a and, for example, may be obtained by deforming the shape by a magnification other than the magnification a in the thickness direction. For example, the deformed shape may be a distorted shape maintaining the shape in the thickness direction or deformed by a magnification larger than the magnification a in order to conversely emphasize the shape. Here, in addition to the distorted shape, the deformed shape includes a shape deformed on a scale that is the same as an actual scale.

[S5: X-ray Measurement Optical System Modeling Step]

Next, the description of the steps of the first embodiment is continued referring back to FIG. 3. The X-ray measurement optical system modeling portion 45 models the deformed shape of the sample, the distorted shape of the propagating X-rays, and each of the deformed shapes of the plurality of X-ray measurement optical system parts (S5: X-ray measurement optical system modeling step). Here, "model" refers to processing of numerically describing the shape, position, and size of an object to be drawn, which are required for image generation by computer graphics (CG). The modeling involves creating a plurality of modeling coordinates which provide the shapes of the sample 100, the propagating X-rays, and each of the plurality of X-ray measurement optical system parts. Here, when the shapes have a curved surface, the curved surfaces may be expressed in the shape of functions by parametric representation, or polyhedral shapes generated by polygonal representation may be smoothly processed as subdivision surfaces.

The distorted shape of the propagating X-rays includes the distorted shape of the incident X-rays and the distorted shape of the scattered X-rays. The deformed shapes of the plurality of X-ray measurement optical system parts include the distorted shape of the first incident-side optical part, the distorted shape of the first scattered-side optical part, and each of the deformed shapes of the other X-ray measurement optical system parts.

[S6: X-ray Measurement Optical System Rendering Step]

The X-ray measurement optical system rendering portion 46 renders the numerical description (numerical data) related to the deformed shape of the sample, the distorted shape of the propagating X-rays, and each of the deformed shapes of the plurality of X-ray measurement optical system parts, which are modeled in the X-ray measurement optical system modeling step S5 (X-ray measurement optical system rendering step S6). Here, "render" refers to processing of generating a two-dimensional digital image from a state described as numerical data. For example, a photo-realistic image may be generated by ray tracing (tracing rays of light).

[S7: Display Instruction Step]

The display instruction portion 47 gives an instruction to display the two-dimensional digital image generated in the X-ray measurement optical system rendering step S6 as a display image (display instruction step S7). The information output portion 14 of the control unit 4 instructs the display device 6 to display the two-dimensional digital image in the display part DA of the display information input screen (see FIG. 7).

The display image displayed in the display part DA may be graphical projections in a variety of different directions. The user can freely rotate (the respective parts of) the X-ray measurement optical system displayed in the display image by a pointer or the like to display the graphical projections in a variety of different directions.

The user looks at the display image displayed in the display part DA to determine whether or not another setting is required. More specifically, the user determines whether or not change of the angular placement or change of the magnification is required. When both the angular placement and the sample magnification are to be changed, the processing returns to the display information acquisition step S3. Specifically, the user inputs a new value to the angular placement input window or the magnification input window of the display information input screen (see FIG. 7) and clicks the OK button. The display information acquisition portion 43 then newly acquires the magnification and the information on the angular placement. Based on the magnification and the information on the angular placement, the distorted shape determination step S4, the X-ray measurement optical system modeling step S5, the X-ray measurement optical system rendering step S6, and the display instruction step S7 are performed again. When a new angular placement or magnification is not required, the user clicks the cancel button, thereby ending the control program 31.

The operation guide method for the X-ray analysis apparatus 1 (or the operation guide system 3) according to the first embodiment is described above. A main feature of the operation guide system according to the first embodiment is the distorted shape of the incident X-rays and the distorted shape of the scattered X-rays, which are determined by incident X-ray shape deformation means and scattered X-ray shape deformation means, respectively. Through generation of the display image based on those distorted shapes, even a user unfamiliar with X-ray analysis is able to easily understand the shape of the propagating X-rays. In particular, the user can easily understand how the sample is irradiated by the incident X-rays and how the scattered X-rays are generated from the sample.

Figure 10B:
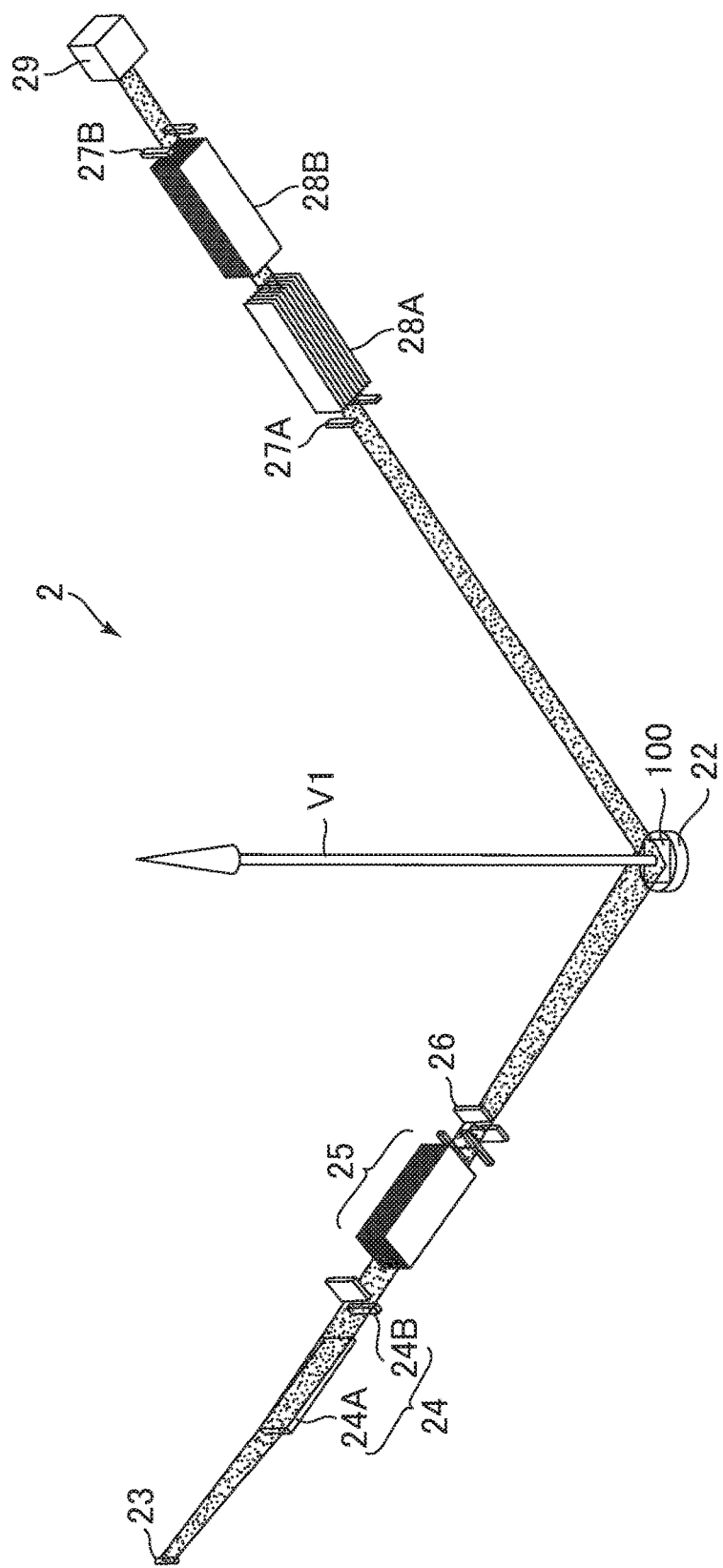
FIG. 10B is a display image according to the first embodiment of the present invention.
Figure 10C:
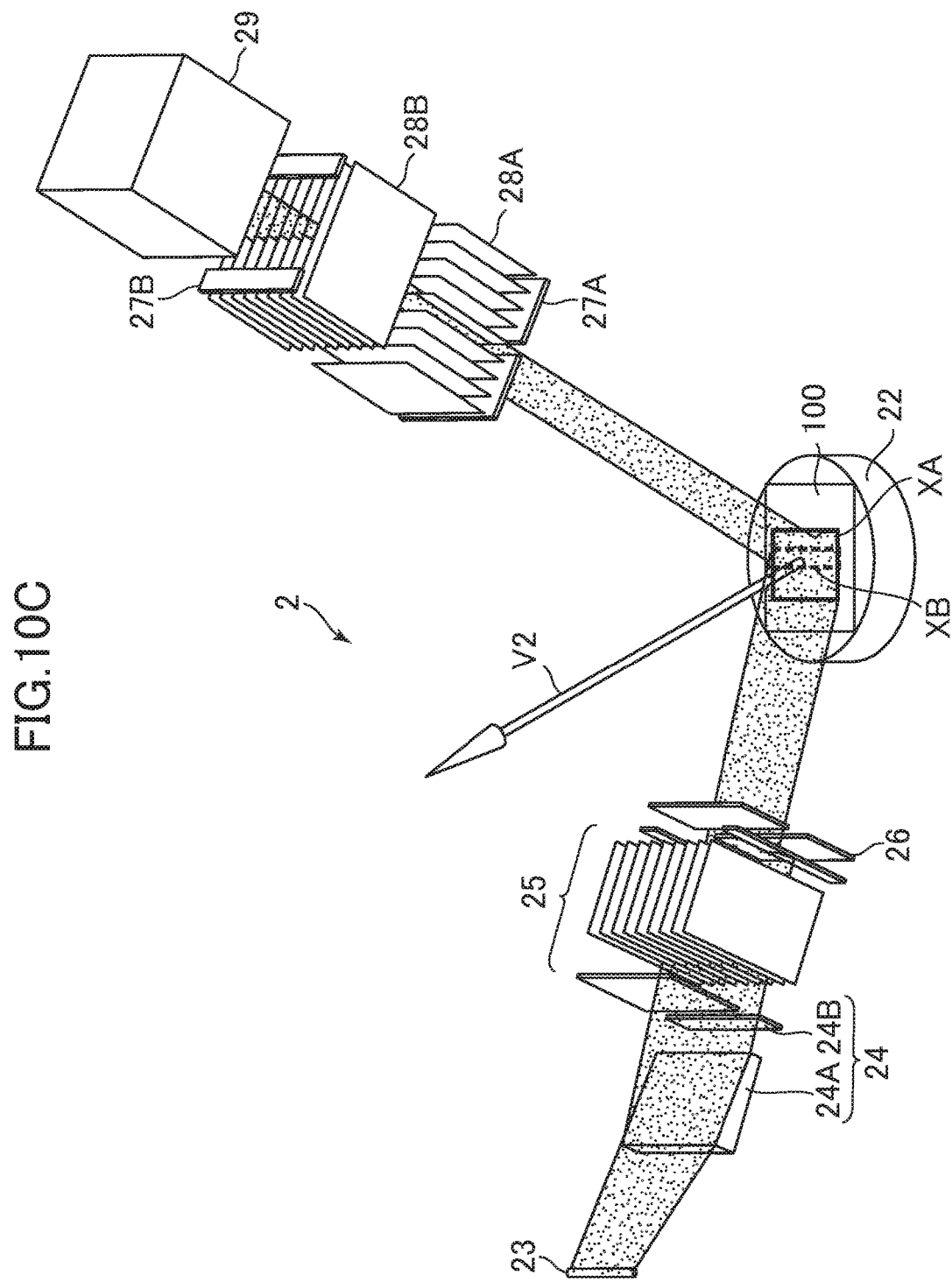
FIG. 10C is a display image according to the first embodiment of the present invention.

FIG. 10A to FIG. 10C are each an illustration of the display image according to the first embodiment. FIG. 10A is an illustration of a case in which the magnification a is a=5, and the angular placement θ of the sample is θ=20°. FIG. 10B is an illustration of a case in which the angular placement is the same as that of FIG. 10A, but the magnification a is a=1 (same scale). FIG. 10C is an illustration of a case in which the magnification is the same as that of FIG. 10A, but the angular placement θ is 9=30°.

In FIG. 10B, the scale of the X-ray measurement optical system matches the actual scale of an X-ray measurement optical system, and hence the relative positions of the X-ray measurement optical system parts are easy to understand, but it is difficult for the user to grasp the shape of the propagating X-rays. In contrast, in FIG. 10A, the sample 100 is magnified by the magnification, and the shapes of the propagating X-rays and the X-ray measurement optical system parts are magnified by the magnification in the plane perpendicular to the optical axis direction of the X-ray while being maintained in the optical axis direction of the X-ray. Due to this, the user can easily understand the shape of the propagating X-rays. In particular, an irradiated region XA in which the sample 100 is irradiated by the incident X-rays and a detection region XB in which the scattered X-rays generated from the sample 100 is detected are displayed, and the irradiated region XA and the detection region XB match each other. The irradiated region XA and the detection region XB are included in (a surface of) the sample 100. The detection region XB and the irradiated region XA match each other, and hence it is easy for the user to visually understand that a desired measurement can be performed at the angular placement. Through use of the distorted shapes in this way, each of the shapes of the X-ray measurement optical system parts are displayed in an exaggerated manner, but the user can understand the measurement state of the X-ray measurement optical system without feeling that the shapes are so exaggerated as to uncomfortably stand out. In FIG. 10A and FIG. 10B, a scattering vector V1 determined from the optical axis of the incident X-rays which irradiate the sample and the optical axis of the scattered X-rays generated from the sample is illustrated. The vector V1 is calculated by the distorted shape determination portion 44, and then modeled by the X-ray measurement optical system modeling portion 45.

In FIG. 10C, in comparison to FIG. 10A, the value of the angular placement θ is large. Through change of the angular placement θ, the irradiated region XA and the detection region XB change. As illustrated in FIG. 10C, in response to the sample being magnified by the magnification a, the irradiated region XA and the detection region XB are magnified such that the user can easily understand how the incident X-rays irradiate the sample 100. The irradiated region XA and the detection region XB are included in (the surface of) the sample 100. Further, the detection region XB is included in the irradiated region XA and a sufficient width is secured between the two regions, and hence it is easy for the user to visually recognize that desired measurement can be performed at the current angular placement. Similarly, in FIG. 10C, a scattering vector V2 determined from the optical axis of the incident X-rays and the optical axis of the scattered X-rays is illustrated.

Figure 11:
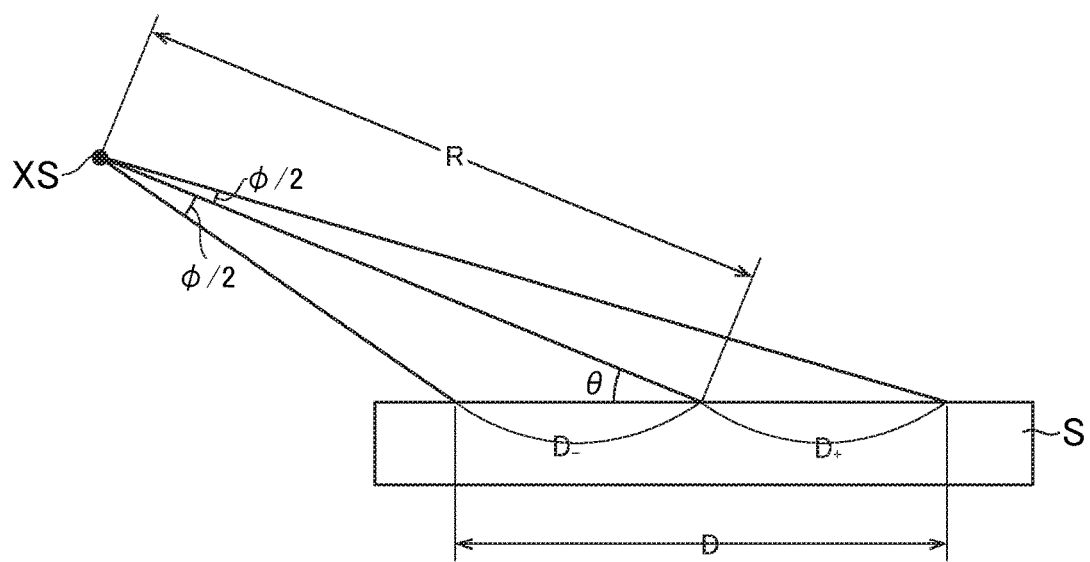
FIG. 11 is a diagram for illustrating approximation of the shape of the propagating X-rays.

FIG. 11 is a diagram for illustrating approximation of the shape of the propagating X-rays. The propagating X-rays may include divergent X-rays, parallel X-rays, focusing X-rays, or any other similar X-ray. In FIG. 11, for brevity of description, a case in which a divergent X-ray emitted from a point X-ray source XS irradiates a sample S is illustrated as an example of the divergent X-ray. Assuming that a viewing angle of the divergent X-ray that diverges to the sample from the point X-ray source XS is θ, an angle formed by an outer edge of the X-ray and the optical axis of the X-ray is θ/2. Assuming that an angle formed by the optical axis of the X-ray and the sample S is θ, a length D is defined as $D=D_-+D_+$. The length D is the length of irradiation of the sample S by the X-ray. Here, $D_-$ and $D_+$ are described by Equation 1 and Equation 2, respectively.

$$D_-=R \sin \varphi \cdot \{1/\sin(\theta+\varphi/2)\} \quad \text{(Equation 1)}$$

$$D_+=R \sin \varphi \cdot \{1/\sin(\theta-\varphi/2)\} \quad \text{(Equation 2)}$$

Therefore, the length D is described in Equation 3.

$$D=D_-+D_+=R \sin \varphi \cdot \{1/\sin(\theta+\varphi/2)+1/\sin(\theta-\varphi/2)\} \quad \text{(Equation 3)}$$

Under a state in which R, which is the length of the X-ray in the optical axis direction, is maintained to be constant, the sample S is magnified by the magnification a, and the shape of the X-ray is magnified by the magnification a in the plane perpendicular to the optical axis direction of the X-ray to deform the shape of the X-ray. At this time, D changes to aD, and φ changes to aφ. However, when φ is sufficiently small, D is approximated by Equation 4.

$$D \approx (2R\varphi/\sin \theta) \cdot \{1+O(\varphi^2)\} \quad \text{(Equation 4)}$$

Equation 4 holds true even when D and φ are magnified by a times, respectively. In other words, when φ is sufficiently small, D and φ do not change in response to the change described above. When φ in both the incident X-rays and the scattered X-rays is 0 (parallel) or sufficiently small, the present invention can be applied to the shape of the incident X-rays and the shape of the scattered X-rays. In this case, as the state in which φ is sufficiently small, it is desired that φ (rad) be equal to or less than 0.2, and more desired that φ (rad) be equal to or less than 0.1.

Second Embodiment

Figure 12:
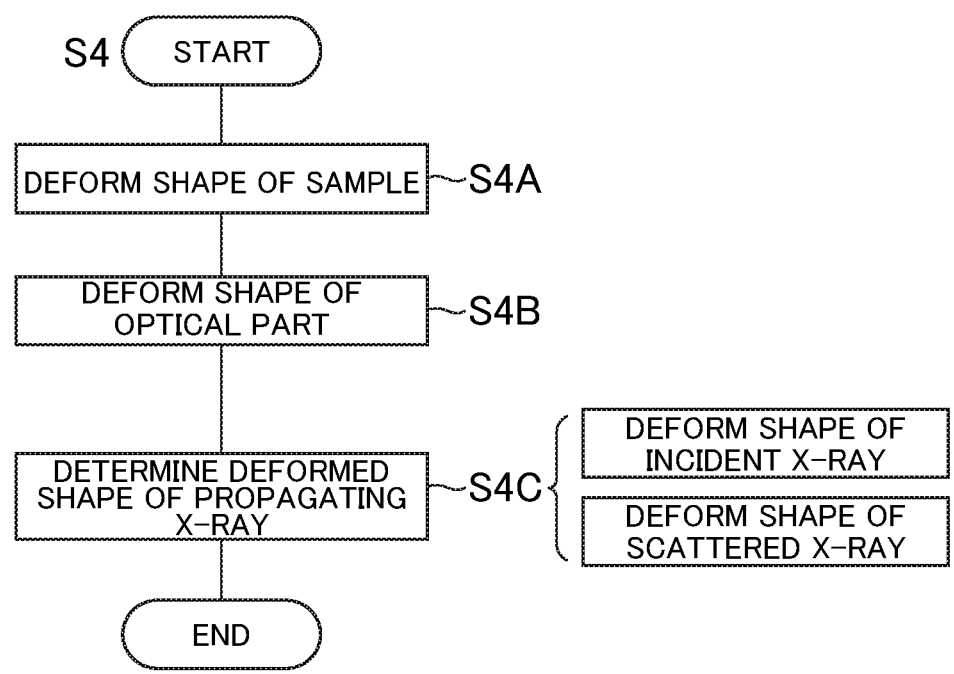
FIG. 12 is a flowchart of a distorted shape determination step according to a second embodiment of the present invention.

FIG. 12 is a flowchart of the distorted shape determination step S4 according to a second embodiment of the present invention. The second embodiment is the same as the first embodiment except that the distorted shape determination step S4 is different. The distorted shape determination portion 44 according to the second embodiment includes a sample shape deformation portion 44A, an optical part shape deformation portion 44B, and a propagating X-ray deformed shape determination portion 44C. The distorted shape determination step S4 according to the second embodiment includes a sample shape deformation step S4A, an optical part shape deformation step S4B, and a propagating X-ray deformed shape determination step S4C.

[S4A: Sample Shape Deformation Step]

In the sample shape deformation step S4A, the sample shape deformation portion 44A magnifies the shape of the sample based on the magnification to determine the deformed shape of the sample. The sample shape deformation step S4A is the same as the sample shape deformation step S4b according to the first embodiment.

[S4B: Optical Part Shape Deformation Step]

In the optical part shape deformation step S4B, the optical part shape deformation portion 44B determines each of the distorted shapes of the plurality of X-ray measurement optical system parts, the distorted shapes being obtained by magnifying respective shapes of the plurality of X-ray measurement optical system parts based on the magnification in a plane perpendicular to the optical axis direction of an X-ray which propagates through the plurality of X-ray measurement optical system parts (optical part shape deformation step S4B). The optical part shape deformation step S4B includes the first incident-side optical part shape deformation step S4e and the first scattered-side optical part shape deformation step S4f according to the first embodiment, and may further include the other optical part shape deformation step S4g according to the first embodiment.

In the first embodiment, in the propagating X-ray shape determination step S4a, the shape of the incident X-rays and the shape of the scattered X-rays are determined. Therefore, the incident optical axis direction of the incident X-rays and the scattered optical axis direction of the scattered X-rays are already determined based on the shape of the incident X-rays and the shape of the scattered X-rays. However, in the second embodiment, the shape of the incident X-rays and the shape of the scattered X-rays are not determined. Therefore, in the optical part shape deformation step S4B, the optical axis of the propagating X-rays may be approximately determined based on the positions of the plurality of X-ray measurement optical system parts to be selected. Further, when strict calculation is required, the optical part shape deformation step S4B may further include the propagating X-ray shape determination step S4a according to the first embodiment to determine the optical axis of the propagating X-rays by the propagating X-ray shape determination step S4a.

[S4C: Propagating X-ray Deformed Shape Determination Step]

In the propagating X-ray deformed shape determination step S4C, the propagating X-ray deformed shape determination portion 44C determines the distorted shape of the propagating X-rays based on the deformed shape of the sample determined in the sample shape deformation step S4A and each of the distorted shapes of the plurality of X-ray measurement optical system parts determined in the optical part shape deformation step S4B.

The propagating X-ray deformed shape determination step S4C includes the incident X-ray shape deformation step and the scattered X-ray shape deformation step. In the incident X-ray shape deformation step, similarly to the incident X-ray shape deformation step S4c according to the first embodiment, the distorted shape of the incident X-rays is determined, the distorted shape being obtained by magnifying the shape of the incident X-rays based on the magnification in the plane perpendicular to the incident optical axis direction of the incident X-rays which irradiates the sample. However, in contrast to the first embodiment in which the shape of the incident X-rays is magnified to determine the distorted shape of the incident X-rays, in the incident X-ray shape deformation step according to the second embodiment, the shape of the incident X-rays is determined based on the deformed shape of the sample and each of the distorted shapes of the plurality of X-ray measurement optical system parts. In this case, the shape of the incident X-rays determined based on the deformed shape of the sample and each of the distorted shapes of the plurality of X-ray measurement optical system parts is the distorted shape of the incident X-rays.

The same applies to the scattered X-ray shape deformation step. In the scattered X-ray shape deformation step according to the second embodiment, the shape of the scattered X-rays is determined based on the deformed shape of the sample and the distorted shapes of the plurality of X-ray measurement optical system parts. In this case, the shape of the scattered X-rays determined based on the deformed shape of the sample and the distorted shapes of the plurality of X-ray measurement optical system parts is the distorted shape of the scattered X-rays.

The X-ray analysis apparatus, the operation guide system therefor, the operation guide method therefor, and the operation guide program therefor according to the embodiments of the present invention have been described above. The present invention is not limited to the above-mentioned embodiments, and can be widely applied. For example, it should be understood that the analysis purpose of the X-ray analysis apparatus is not limited to the above-mentioned four analysis purposes. Further, the plurality of X-ray measurement optical system parts stored in the system information storage portion 33 are limited to ones that can be achieved by parts possessed by the user. However, for example, the stored X-ray measurement optical system may include parts that can be achieved by parts not possessed by the user.

In the X-ray measurement optical system according to the above-mentioned embodiments, the incident X-rays that enter the sample 100 is collimated parallel X-rays. However, the incident X-rays are not limited to the parallel X-rays, and may be focusing X-rays focused toward the sample 100. In this case, the viewing angle φ facing the X-ray source side (for example, the incident slit 26) from the sample 100 is considered. In the above-mentioned embodiments, when the incident X-rays are the parallel X-rays, the viewing angle φ is substantially 0, but the viewing angle φ also sufficiently small when the incident X-rays are the focusing X-rays. The size (vertical length or horizontal length) of the cross section of the X-ray emitted from the incident slit 26 with respect to the distance between the incident slit 26 and the sample 100 is sufficiently small even when compared to a case in which φ is 0.1, and therefore the approximation holds true. The same applies to the scattered X-rays. The scattered X-rays generated from the sample 100 are the parallel X-rays or the divergent X-rays. The viewing angle φ facing the detector side (for example, the first light-receiving slit 27A) from the sample 100 is considered. When the scattered X-rays are the parallel X-rays, the viewing angle θ is substantially 0, but the viewing angle φ is also sufficiently small when the scattered X-rays are the divergent X-rays.

Further, in the above-mentioned embodiments, the distorted shape of the propagating X-rays (the incident X-rays and the scattered X-rays) is displayed in the display image displayed in the display part DA, but the information on the propagating X-rays to be displayed is not limited to the shape of the propagating X-rays. Information on the intensity distribution of the propagating X-rays may be displayed in addition to the distorted shape of the propagating X-rays. When displaying the intensity distribution of the X-ray in grayscale, different intensities may be represented by different colors, or may be expressed by different densities of dots. Further, information on resolution may be displayed in addition to the distorted shape of the propagating X-rays.

What is claimed is:

1. An operation guide system for X-ray analysis, comprising at least one microprocessor configured to:

acquire information on a sample, and information on each of a plurality of X-ray measurement optical system parts configured to conduct X-ray analysis on the sample;

acquire a magnification by which the sample is to be magnified for display;

determine a distorted shape of an incident X-ray obtained when the sample is measured through use of the plurality of X-ray measurement optical system parts;

determine a distorted shape of a scattered X-ray obtained when the sample is measured through use of the plurality of X-ray measurement optical system parts; and model a deformed shape of the sample, which is obtained by magnifying a shape of the sample based on the magnification, the distorted shape of the incident X-ray, and the distorted shape of the scattered X-ray, wherein the distorted shape of the incident X-ray is a shape obtained by magnifying a shape of an incident X-ray, which irradiates the sample, based on the magnification in a plane perpendicular to an incident optical axis direction of the incident X-ray, and wherein the distorted shape of the scattered X-ray is a shape obtained by magnifying a shape of a scattered X-ray, which is generated from the sample to be detected, based on the magnification in a plane perpendicular to a scattered optical axis direction of the scattered X-ray.

2. The operation guide system for X-ray analysis according to claim 1, wherein the at least one microprocessor is further configured to determine, based on the acquired information on the sample and the acquired information on each of the plurality of X-ray measurement optical system parts, the shape of the incident X-ray which irradiates the sample and the shape of the scattered X-ray which is generated from the sample to be detected, which are obtained when the sample is measured through use of the plurality of X-ray measurement optical system parts, wherein the at least one microprocessor magnifies, based on the magnification, the determined shape of the incident X-ray in the plane perpendicular to the incident optical axis direction of the incident X-ray, to thereby determine the distorted shape of the incident X-ray, and wherein the at least one microprocessor magnifies, based on the magnification, the determined shape of the scattered X-ray in the plane perpendicular to the scattered optical axis direction of the scattered X-ray, to thereby determine the distorted shape of the scattered X-ray.

3. The operation guide system for X-ray analysis according to claim 2, wherein the plurality of X-ray measurement optical system parts comprise a first incident-side optical part arranged closest to the sample on an incident side of the sample, and a first scattered-side optical part arranged closest to the sample on a scattered side of the sample, wherein the at least one microprocessor is further configured to:

determine a distorted shape of the first incident-side optical part, the distorted shape being obtained by magnifying a shape of the first incident-side optical part based on the magnification in the plane perpendicular to the incident optical axis direction of the incident X-ray; and determine a distorted shape of the first scattered-side optical part, the distorted shape being obtained by magnifying a shape of the first scattered-side optical part based on the magnification in the plane perpendicular to the scattered optical axis direction of the scattered X-ray, and wherein the at least one microprocessor models the distorted shape of the first incident-side optical part and the distorted shape of the first scattered-side optical part.

4. The operation guide system for X-ray analysis according to claim 1, wherein the plurality of X-ray measurement optical system parts comprise a first incident-side optical part arranged closest to the sample on an incident side of the sample, and a first scattered-side optical part arranged closest to the sample on a scattered side of the sample, wherein the at least one microprocessor is further configured to:

determine a distorted shape of the first incident-side optical part, the distorted shape being obtained by magnifying a shape of the first incident-side optical part based on the magnification in the plane perpendicular to the incident optical axis direction of the incident X-ray; and determine a distorted shape of the first scattered-side optical part, the distorted shape being obtained by magnifying a shape of the first scattered-side optical part based on the magnification in the plane perpendicular to the scattered optical axis direction of the scattered X-ray, and wherein the at least one microprocessor models the distorted shape of the first incident-side optical part and the distorted shape of the first scattered-side optical part.

5. The operation guide system for X-ray analysis according to claim 1, wherein the at least one microprocessor is further configured to determine each of distorted shapes of the plurality of X-ray measurement optical system parts, the distorted shapes being obtained by magnifying respective shapes of the plurality of X-ray measurement optical system parts based on the magnification in a plane perpendicular to an optical axis direction of an X-ray which propagates through the plurality of X-ray measurement optical system parts, wherein the at least one microprocessor determines the distorted shape of the incident X-ray based on the acquired information on the sample and the determined distorted shapes of the plurality of X-ray measurement optical system parts determined, and wherein the at least one microprocessor determines the distorted shape of the scattered X-ray based on the acquired information on the sample and the determined distorted shapes of the plurality of X-ray measurement optical system parts.

6. The operation guide system for X-ray analysis according to claim 1, wherein the at least one microprocessor maintains the shape of the incident X-ray in the incident optical axis direction of the incident X-ray, and wherein the at least one microprocessor maintains the shape of the scattered X-ray in the scattered optical axis direction of the scattered X-ray.

7. The operation guide system for X-ray analysis according to claim 1, wherein the at least one microprocessor is further configured to acquire information on an angular placement of the sample, wherein the at least one microprocessor determines the distorted shape of the incident X-ray further based on the information on the angular placement, and wherein the at least one microprocessor determines the distorted shape of the scattered X-ray further based on the information on the angular placement.

8. An operation guide method for X-ray analysis, the operation guide method comprising:

acquiring information on a sample and information on each of a plurality of X-ray measurement optical system parts configured to conduct X-ray analysis on the sample;

acquiring a magnification by which the sample is to be magnified for display;

determining a distorted shape of an incident X-ray obtained when the sample is measured through use of the plurality of X-ray measurement optical system parts;

determining a distorted shape of a scattered X-ray obtained when the sample is measured through use of the plurality of X-ray measurement optical system parts; and modeling a deformed shape of the sample, which is obtained by magnifying a shape of the sample based on the magnification, the distorted shape of the incident X-ray, and the distorted shape of the scattered X-ray, wherein the distorted shape of the incident X-ray is a shape obtained by magnifying a shape of an incident X-ray, which irradiates the sample, based on the magnification in a plane perpendicular to an incident optical axis direction of the incident X-ray, and wherein the distorted shape of the scattered X-ray is a shape obtained by magnifying a shape of a scattered X-ray, which is generated from the sample to be detected, based on the magnification in a plane perpendicular to a scattered optical axis direction of the scattered X-ray.

9. A program stored in a non-transitory computer-readable recording medium executed by a computer, to perform a function of:

acquire information on a sample, and information on each of a plurality of X-ray measurement optical system parts configured to conduct X-ray analysis on the sample;

acquiring a magnification by which the sample is to be magnified for display;

determining a distorted shape of an incident X-ray obtained when the sample is measured through use of the plurality of X-ray measurement optical system parts;

determining a distorted shape of a scattered X-ray obtained when the sample is measured through use of the plurality of X-ray measurement optical system parts; and modeling a deformed shape of the sample, which is obtained by magnifying a shape of the sample based on the magnification, the distorted shape of the incident X-ray, and the distorted shape of the scattered X-ray, wherein the distorted shape of the incident X-ray is a shape obtained by magnifying a shape of an incident X-ray, which irradiates the sample, based on the magnification in a plane perpendicular to an incident optical axis direction of the incident X-ray, and wherein the distorted shape of the scattered X-ray is a shape obtained by magnifying a shape of a scattered X-ray, which is generated from the sample to be detected, based on the magnification in a plane perpendicular to a scattered optical axis direction of the scattered X-ray.

* * * * *